United States Patent [19]

Rosen et al.

[11] Patent Number: 4,953,562

[45] Date of Patent: Sep. 4, 1990

[54] METHOD OF URINE SPECIMEN IDENTIFICATION

[76] Inventors: Fred Rosen, 8069 Caminito Mallorea, La Jolla, Calif. 92307; Bernard Rimland, 4182 Adams Ave., San Diego, Calif. 92116

[21] Appl. No.: 267,197

[22] Filed: Nov. 4, 1988

[51] Int. Cl.$^5$ .............................................. A61B 5/00
[52] U.S. Cl. ....................................... 128/771; 436/56
[58] Field of Search ..................... 128/760, 771, 632; 436/56; 600/3, 4

[56] References Cited

U.S. PATENT DOCUMENTS

| | | | |
|---|---|---|---|
| 3,451,778 | 6/1969 | Fearon | 436/56 |
| 3,733,178 | 5/1973 | Eriksen | 436/56 |
| 4,223,004 | 9/1980 | Hsia et al. | 436/56 |

FOREIGN PATENT DOCUMENTS 0695661  11/1979  U.S.S.R. .............................. 128/771

Primary Examiner—Max Hindenburg
Attorney, Agent, or Firm—Lawrence Rosen

[57] ABSTRACT

The invention includes a method of, and substances for use in the method of, identifying the source of a urine sample to be collected for biochemical analysis including administering to a person or animal whose urine is to be tested a formulation containing predetermined portions of one or more identifying substances that are vitamins, maintaining an identification of the formulations so that the person or animal to which it was administered and a urine collecting means can be identified, obtaining a urine sample from the person or animal in the urine collecting means, and analyzing the urine sample for the presence of the identifying substances or their metabolites.

7 Claims, No Drawings

METHOD OF URINE SPECIMEN IDENTIFICATION

BACKGROUND OF THE INVENTION

1. Field of the Invention

The invention described and claimed herein relates to urinalysis and particularly to a method of identifying urine samples. More particularly, it relates to identifying the source of urine samples collected for biochemical analysis where there is potential for laboratory error or deceptive substitution of one urine specimen for another.

2. Description of Related Art

Known analysis techniques can give quantitative and qualitative indications of the concentration of a drug or other biological or chemical substance in a biological specimen. There are, however, possibilities for error at various steps in these testing processes. For example, because the validity of the biochemical analysis depends upon whether the specimen submitted is indeed that of the individual in question, the collection and custody of the sample itself must be closely monitored. Until now, no analytic technique has been described that can positively identify or confirm the source of the specimen.

The patent literature includes a labelling system for clinical laboratory specimens as described in U.S. Pat. No. 3,733,178 to Eriksen, entitled "Chemical Coding Method". According to the disclosed method, known amounts of inert chemicals are added to specimens after collection, so that at the time, the specimens are analyzed, the chemical identifiers disclose concentrations uniquely associated with the sample. Another method of chemical labeling is disclosed in U.S. Pat. No. 3,451,778 to Fearson, entitled "Method of Labeling." According to this method, substances are labeled by the addition of a chemical compound of a noble gas. Thereafter, these noble gases may be detected to identify the substance to which they have been added.

U.S. Pat. No. 4,223,004 to Hsia et al., filed May 23, 1977, entitled "Drug Compositions", describes a method for detecting whether a drug addict patient in a maintenance therapy program has supplemented his prescribed dosage of a drug with drugs obtained from another source. The patient consumes drug compositions containing known proportions of a drug and its isotopic analogue. If the patient is in compliance with the maintenance program, analysis of the patient's urine or blood should reveal ratios that are the same as those in the drug prescribed.

The labeling methods in the art described above, relate either to labeling of specimens after collection to insure against subsequent mishandling or to detecting whether an individual supplemented his drug dosage from another source. None, however, will indicate whether there has been a deceptive or mistaken substitution of one urine for another. We have invented and describe herein a method for urine specimen identification utilized before collection for the purpose of positively identifying its source.

SUMMARY OF THE INVENTION

In a method of urine specimen identification described and claimed herein the individual whose urine is to be tested is asked to consume in the presence of one or more trusted witnesses, or is given by injection or otherwise, one or more formulations, including tablets, capsules, powders or liquids, containing one or more harmless identifying substances that can be rapidly absorbed by the body and will quickly appear in the urine. With knowledge of which substances were consumed by or introduced into the individual, the collected urine may later be analyzed for the presence of these substances or the metabolic products of these substances. Thus, through analysis of the urine, it is possible to determine the source of the specimen and detect any deliberate or accidental substitution by the laboratory or by the individual. There are numerous applications of the present method, which will be described more fully in the detailed description which follows.

DETAILED DESCRIPTION OF THE INVENTION

The invention comprises a method for identifying the source of urine samples collected for biochemical analysis. Identification is accomplished by introducing into the individual whose urine is to be analyzed, or having the individual consume, in the presence of one or more trusted witnesses, one or more formulations such as tablets, capsules or liquids containing harmless identifying substances in predetermined proportions. After administration, these substances are rapidly absorbed by the body and will appear very quickly in the urine. The amount and character of each substance detected in the collected urine sample will reflect the amount and character of substances contained in the formulation, e.g., tablet, capsule, etc. Since the laboratory knows which formulation was given to a particular individual, detection of the corresponding proportions of substances in the urine will assure that the biochemical findings derived from the specimen are applicable to the individual in question, and not to another individual. If the specimen collected fails to show the expected profile, there would be reason for suspicion and retesting.

This method has particular utility for reducing error where there is potential for mishandling of specimens by the laboratory as well as for detecting deliberate substitution of one urine specimen for another in drug detection programs, drug treatment programs, athletic events, horse races or medical examinations for life or health insurance purposes. In the case of humans, this procedure eliminates the inconvenience, embarrassment and cost of having a witness accompany each person being tested to the restroom to insure that the urine specimen was produced by the individual being tested.

More particularly, the method of this invention incorporates into a tablet, capsule, or fluid, for example, one or more identifying substances that will induce a specific profile or ratio in the urine. The number of different formulations required to drastically reduce or eliminate the danger of substitution among a number of individuals would depend on the size of the population screened. The incorporated substances should have certain characteristics. Preferably, they should be harmless, easily absorbed by the body, quickly excreted in the urine, and identifiable in the urine. Ideally, the substances should not be normally present in the urine in amounts capable of compromising the identification process.

The particular identifying substances that may be used must be harmless and are preferably included on the FDA's "Generally Recognized As Safe" list (GRAS), which is incorporated herein by reference. The substances used in the method of this invention are certain vitamins and their metabolites. They are used in amounts ranging from 25 to 100 mgs. or in greater amounts sufficient to be detected by methods such as NMR spectroscopy and gas chromatography/mass spectometry (GC/MS).

Detection and determination of the amounts of the identifying substances in the urine may be accomplished by standard laboratory instruments. Of course, the method of analysis depends on the type of substance utilized. It also might be necessary to have two types of urine identification, one that is rapid and less costly to perform and a secondary analysis which is more accurate, but more expensive and difficult to perform. The initial test of, for example, combinations of certain vitamins, could be detected by their fluorescence, while a second test could be GC/MS detection of the same vitamins specially synthesized to contain a rare or unusual isotope of an atom in the molecule. The thiamine, riboflavin, niacinamide, and pyridoxine vitamins or their metabolites, for example, will normally be present in urine. However, by using ratios of different vitamins, by marked dilution of the urine due to ingestion of fluids, by collecting the urine within two hours, it will be possible to clearly identify the urine specimen. The subjects can also be questioned as to whether they are presently taking vitamins and allowance for such vitamin supplementation can be taken into account.

The following illustrates the manner in which our urine identification method may operate. As an athlete enters the locker room he is approached by the manager of the team who is well acquainted with each of the team members and a testing officer who has a list of the names of each team member and a collection of sealed and serial-numbered envelopes containing tablets with identifying vitamins or their metabolites. The testing officer randomly picks out an envelope, copies down the serial number after the player's name and requests him to open the envelope and swallow the tablet in the presence of the testing officer and team manager. The player is then requested to collect a urine sample after about 30–120 minutes in a bottle (or other fluid retaining vessel or fluid collection apparatus) labeled with the same serial number. When the sample is subjected to biochemical analysis, the sample is tested to make sure it contains the exact combination of known vitamin(s) that had been in the consumed tablet. If the sample does in fact belong to the player, the pattern of substances detected in the urine should match the expected pattern for that tablet. If, for example, the tablet that the player consumed contained a large amount of harmless substance A, a moderate amount of harmless substance B, and zero quantities of harmless substances C and D, analysis of the collected urine sample would disclose this specific pattern of identifying substances, indicating that the urine specimen submitted by the player was in fact his own.

If traces of cocaine and/or marijuana are found in the urine sample with the serial number assigned to the player, the player may protest that the lab or someone must have mixed up the urine samples. Because the manager and testing officer both witnessed his consumption of the tablet containing the predetermined amounts of vitamins or their metabolites and those amounts were found in the urine sample attributed to the player, an excuse that the urine samples were mixed up is insupportable.

If the urine sample is evaluated and found to contain no traces of cocaine, marijuana or any other drug, but the pattern of substances in the tablet that the player consumed does not match that found in the urine, this would indicate that the specimen bottle did not contain the player's urine but the urine of someone else. Further, by checking the records, it can be established whether another person on the team had injested the tablet with the pattern found.

The following are examples of useful vitamin markers and particular amounts thereof:
(1) Thiamine, 25 mg
(2) Riboflavin, 25 mg
(3) Niacinamide, 50 mg
(4) Pyridoxine, 50 mg
(5) Thiamine, 25 mg + Riboflavin, 25 mg
(6) Thiamine, 25 mg + Niacinamide, 50 mg
(7) Thiamine, 25 mg + Pyridoxine, 50 mg
(8) Riboflavin, 25 mg + Niacinamide, 50 mg
(9) Riboflavin, 25 mg + Pyridoxine, 50 mg
(10) Niacinamide, 50 mg + Pyridoxine, 50 mg
(11) Thiamine, 25 mg; Riboflavin, 25 mg; Niacinamide, 50 mg; Pyridoxine, 50 mg
(12) Riboflavin 25 mg; Niacinamide, 50 mg; Pyridoxine, 50 mg
(13) Thiamine, 25 mg; Niacinamide, 50 mg; Pyridoxine, 50 mg
(14) Thiamine, 25 mg; Riboflavin, 25 mg; Pyridoxine, 50 mg
(15) Thiamine, 25 mg; Riboflavin, 25 mg; Niacinamide, 50 mg The use of the four vitamins (thiamine, riboflavin, niacinamide and pyridoxine) is based on the fact that they are excreted in the urine either unchanged or as a metabolic derivative(s), each of which can be detected either qualitatively or quantitatively by an established fluorometric method. These compounds appear in urine rapidly (1–2 hours), and in sufficient amounts so that the urine could be diluted considerably (1:50 or 1:100) without influencing the results of the assay. Their detection in urine either individually or as a ratio, if one or more vitamins are contained in the formulation, would serve as a signature or identification of that particular urine specimen. It should be noted that the number of the above formulations could be increased simply by altering the amount of vitamin present in the tablet; these vitamins are nontoxic, and much larger amounts than in the example cited above are present in various vitamin products. The advantage of using vitamins for this purpose is that they would be acceptable in terms of safety and extremely sensitive methods, e.g., fluorometric methods, are available for their detection in urine.

Of course, the invention described and claimed herein is useful for animals other than humans, including for example, horses and dogs. The vitamin metabolites are thiochrome, N'-methylnicotinamide and 4-pyridoxic acid.

What is claimed is:

1. A method for identifying the source of a urine sample to be collected for biological or chemical analysis which comprises;
   a. administering to a person or animal whose urine is to be tested a formulation containing predetermined portions of one or more identifying substances selected from the group consisting of thiamine, riboflavin, niacinamide, pyridoxine, and mixtures thereof;
   b. maintaining an identification of said formulation so that said person or animal to which it was administered and a urine collecting means for said person or animal can be identified;

c. obtaining a urine sample from said person or animal in said urine collecting means;

d. analyzing said urine sample for the presence of said identifying substances or their metabolites.

2. The method of claim 1 wherein said formulation comprises a tablet, capsule, powder or liquid.

3. The method of claim 1 wherein said formulation comprises predetermined amounts of from 1 to 4 identifying substances.

4. The method of claim 1 wherein said identifying substances are intermediary metabolites of said vitamins.

5. The method of claim 1 wherein said identifying substances are easily absorbed by the body, are quickly excreted, are identifiable in the urine, and have little or no toxicity.

6. The method of claim 1, wherein said formulation is injected into said person or animal.

7. The method of claim 1 wherein said sample to be collected is to be screened for one or more illicit drugs.

* * * * *